US011517196B2

United States Patent
Su et al.

(10) Patent No.: US 11,517,196 B2
(45) Date of Patent: Dec. 6, 2022

(54) EVALUATION DEVICE FOR TEAR SECRETION

(71) Applicant: YUAN ZE UNIVERSITY, Taoyuan (TW)

(72) Inventors: Tai-Yuan Su, Taoyuan (TW); Tsung-Yen Tsai, Taoyuan (TW); Duan-Yu Chen, Taoyuan (TW)

(73) Assignee: Yuan Ze University, Taoyuan (TW)

(*) Notice: Subject to any disclaimer, the term of this patent is extended or adjusted under 35 U.S.C. 154(b) by 719 days.

(21) Appl. No.: 16/568,509

(22) Filed: Sep. 12, 2019

(65) Prior Publication Data
US 2021/0076933 A1    Mar. 18, 2021

(51) Int. Cl.
*A61B 3/10*    (2006.01)
*A61B 5/01*    (2006.01)
*A61B 3/00*    (2006.01)
*A61B 3/14*    (2006.01)

(52) U.S. Cl.
CPC ............ *A61B 3/101* (2013.01); *A61B 3/0041* (2013.01); *A61B 3/14* (2013.01); *A61B 5/01* (2013.01)

(58) Field of Classification Search
CPC ......... A61B 3/101; A61B 3/0041; A61B 5/01; A61B 3/14
See application file for complete search history.

(56) References Cited

U.S. PATENT DOCUMENTS

| 10,168,791 B2* | 1/2019 | Gribetz | G06F 3/013 |
| 2005/0194876 A1* | 9/2005 | Shimada | A61B 17/0206 313/110 |
| 2012/0172854 A1* | 7/2012 | Raymond | A61F 9/008 606/5 |
| 2015/0196203 A1* | 7/2015 | Abreu | A61B 5/742 600/549 |
| 2016/0069743 A1* | 3/2016 | McQuilkin | G01N 21/255 356/416 |
| 2017/0344109 A1* | 11/2017 | Das | G06F 3/011 |
| 2018/0064950 A1* | 3/2018 | Segal | A61N 2/006 |
| 2019/0175012 A1* | 6/2019 | Millar | A61B 5/14507 |
| 2020/0375451 A1* | 12/2020 | Zavislan | A61B 3/102 |
| 2021/0068655 A1* | 3/2021 | Zhang | A61B 3/103 |

FOREIGN PATENT DOCUMENTS

KR  20160063174   * 11/2014  ........... A61B 3/0083

* cited by examiner

*Primary Examiner* — Congvan Tran
(74) *Attorney, Agent, or Firm* — Rosenberg, Klein & Lee

(57) ABSTRACT

An evaluation device for tear secretion uses an air nozzle and a thermal camera device to cause minor irritations to the eyes and record the temperature changes of the eyes to evaluate the quantity of the tear secretion and to determine whether the subject is able to perform reflex tearing normally or not.

10 Claims, 6 Drawing Sheets

EVALUATION DEVICE FOR TEAR SECRETION

BACKGROUND OF THE INVENTION

1. Field of the Invention

The invention relates to an evaluation device for tear secretion that sends airflows to produce minor irritations to the eyes and observes the temperature changes of the eyes by a thermal camera device, so as to evaluate the ability of tear secretion of the eyes and further apply the results to examination of dry eye diseases.

2. Description of the Related Art

Dry eye disease is the most common disease in clinical ophthalmology. About 10-15% of human population are positively diagnosed. The patients are mostly middle-aged or older, and many of them have been under treatment of glaucoma. Dry eye disease has been diagnosed more and more often due to people spending longer time staring at the computer screens and smart devices, causing less frequent blinking of their eyes and further affecting the tear secretion function of the eyes. Also, there are other influential factors such as air pollution and reactions to medicines. The symptoms of dry eye disease includes dryness, tendency to lassitude, itchiness, the feeling of stinging and sensitivity to light, wind and external irritations. In the long term, the patients would get anxious and depressed, and their daily life would be affected as well. Consequently, there are more and more researches aiming to improve the treatment in dry eye disease.

Since the main reason of dry eye disease is poor quantity of tears in the long term which would cause inflammation of the eyes, traditionally, ophthalmologists would perform the Schrimer's test to evaluate the condition of patients' eyes. The test has test strips disposed between the lower eyelid and the ocular surface of the subjects and after 5 minutes, the wetting of the test strips would be the indicator of the tear quality and the quantity of the subjects. Such test is commonly applied clinically, but it is still invasive and would very likely cause other irritations to the eyes; therefore, it is desired to find a testing method without the shortcomings of such tests.

SUMMARY OF THE INVENTION

It is a primary objective of the present invention to provide an evaluation d for tear secretion that produces minor irritation to the eyes to cause reflex tears. The device further has a thermal camera device to detect and record the temperature changes of the central area of the cornea of the eyes. The result of temperature changes is thereby used for evaluating the amount of tear secretion of the eyes and further decide whether the subjects are able to secrete reflex tears with enough amount of tears.

In order to achieve the above objectives, the evaluation device for tear secretion includes a frame having at least one inner rim for fixing a position of an eye; a channel including an opening at an end thereof, said opening connecting said inner rim of said frame for said channel to be fixedly connecting said frame; a nozzle having an exit end thereof arranged within said channel toward said inner rim of said frame; an air supply device connected to an entry end of said nozzle; a microcomputer electrically connected to said air supply device for operating said air supply device and said nozzle to send airflow from said opening to the eye at said inner rim, thereby producing minor irritation to the eye to see whether there is reflex tearing or not; and a thermal camera device arranged at an end of said channel corresponding to the end with said opening and having an optical camera arranged toward said opening for taking images of the eye with temperature changes thereof during reflex tearing reaction or non-reflex tearing reaction, said thermal camera device being electrically connected to said microcomputer for said microcomputer to analyze the temperature changes and thereby evaluate a secretion of tears of the eye.

The device further includes a screen to be electrically connected to the microcomputer for displaying images of the eye during the operation. The eye has a central area and a surrounding area defined in accordance with the central area; the central area and the surrounding area are memorized by the microcomputer for which to detect and record an average temperature of the surrounding area during operation.

In addition, the surrounding area has a diameter of 3 mm.

The microcomputer has broadcasting function to send instructions of opening and closing of the eye and meanwhile operates the air supply device correspondingly during operation.

Moreover, the microcomputer has a field-programmable gate array.

Furthermore, the position of the nozzle is adjustable for aligning with a position of different eyes. The air supply device is either an air pump or a high-pressured air cylinder. The frame is a glasses frame. The nozzle has an inner diameter of 0.5 mm and an inner surface area of 0.20 mm$^2$, and the nozzle has a volume flow rate of 5 cm$^3$/sec and a wind speed of 2.5 m/sec.

With structures disclosed above, the present invention induces the reflex tears of the eyes by sending a stream of steady airflow to the eyes and having a thermal camera device focusing on the eyes to record the temperature changes of the eyes during the process. When the amount of the reflex tears are enough, the temperature of the eyes drops greater; when the amount of the reflex tears is not enough, the temperature of the eyes drops less. Thereby the present invention is able to provide an indication of whether the function of tear secretion of an eye is well or not.

and

Figure 1:
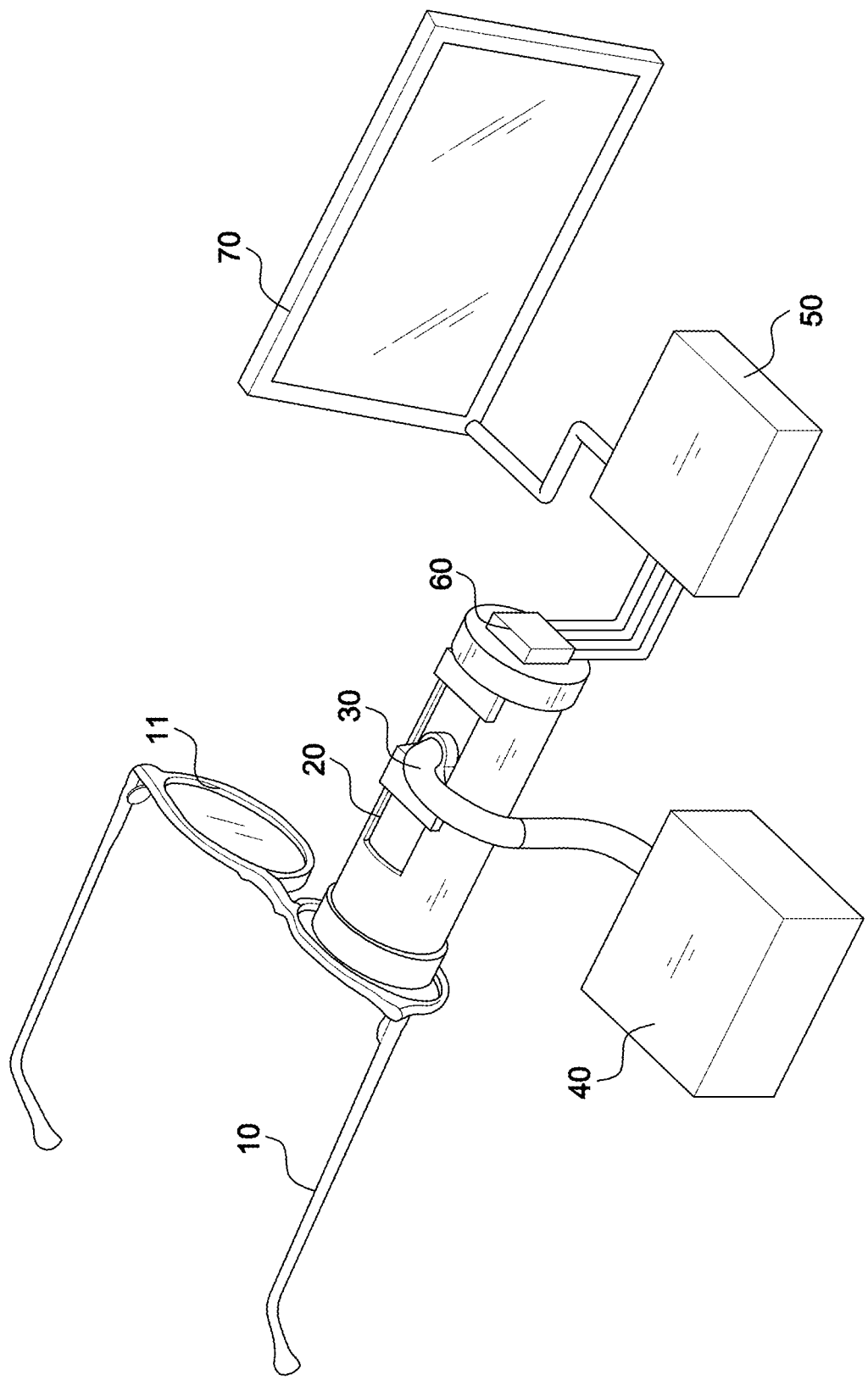
FIG. 1 is a perspective view of the present invention.
Figure 2:
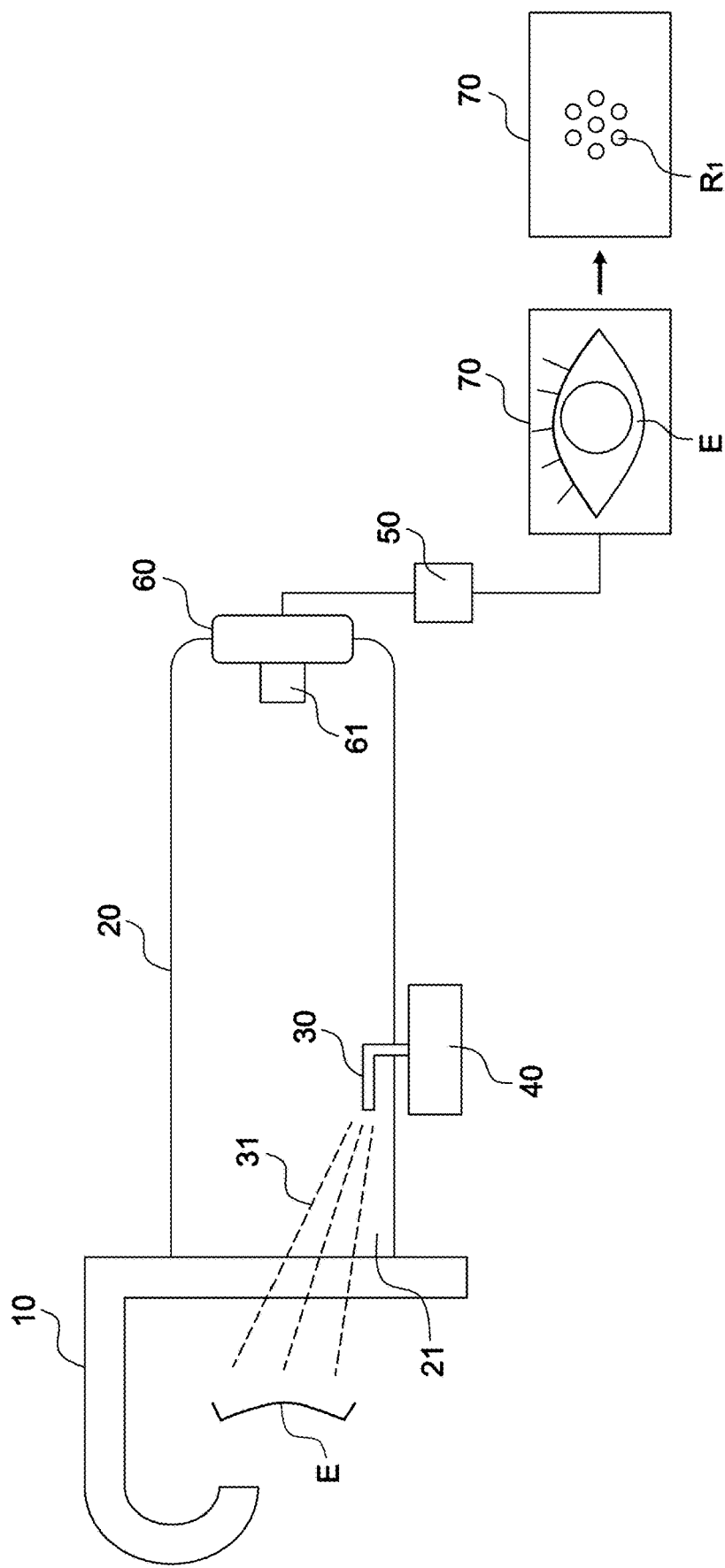
FIG. 2 is a schematic diagram illustrating operation of the present invention.
Figure 3:
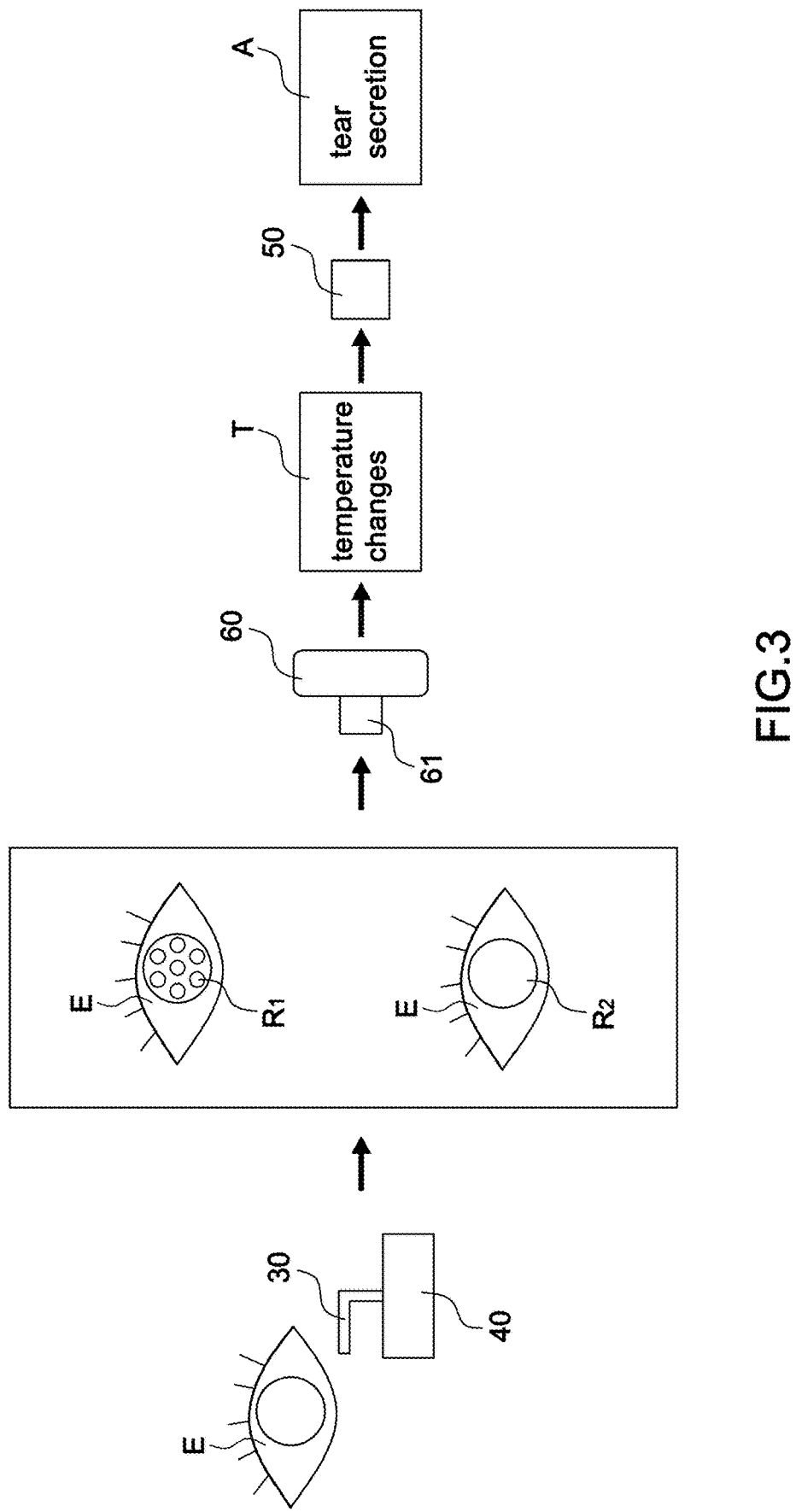
FIG. 3 is a schematic diagram illustrating an evaluation process of tear secretion according to the present invention.
Figure 4:
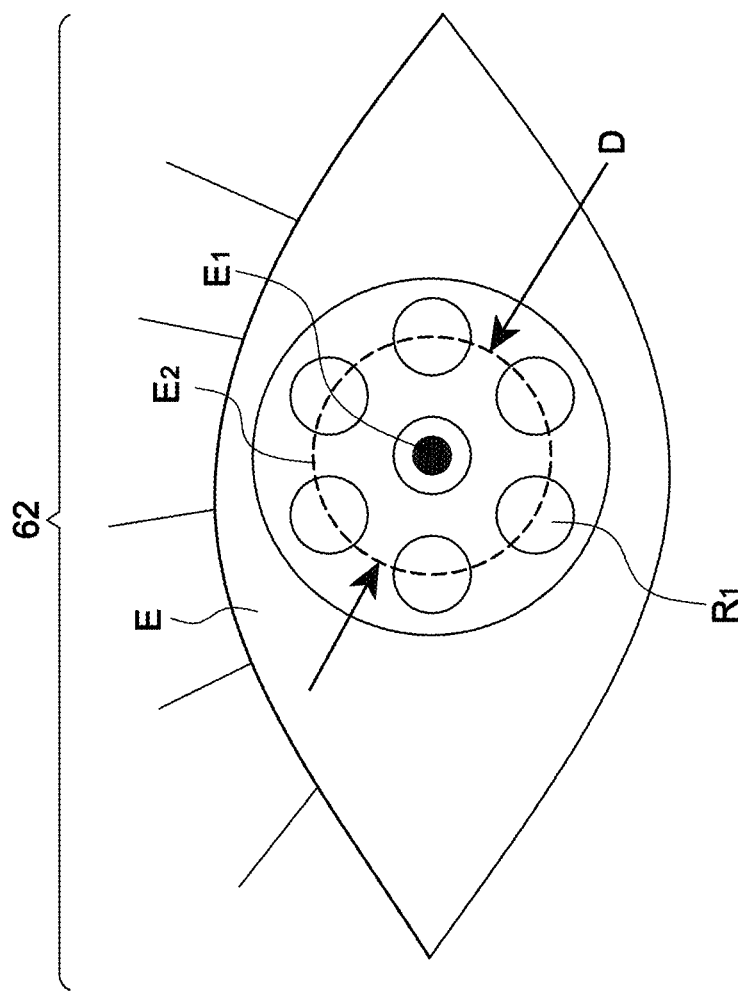
FIG. 4 is a schematic diagram illustrating a calculation process of average temperature within a surrounding area of a central area of an eye according to the present invention.
Figure 5:
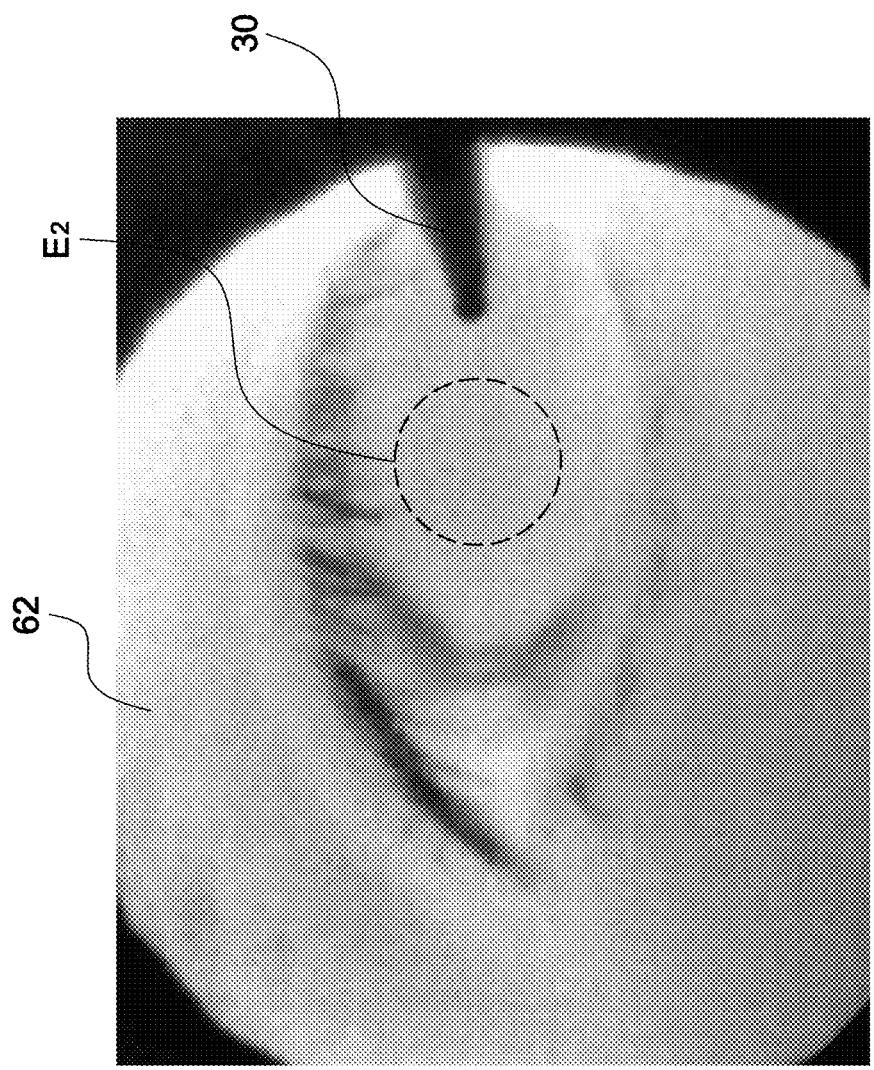
FIG. 5 is a thermal image of an eye according to the present invention.
Figure 6:
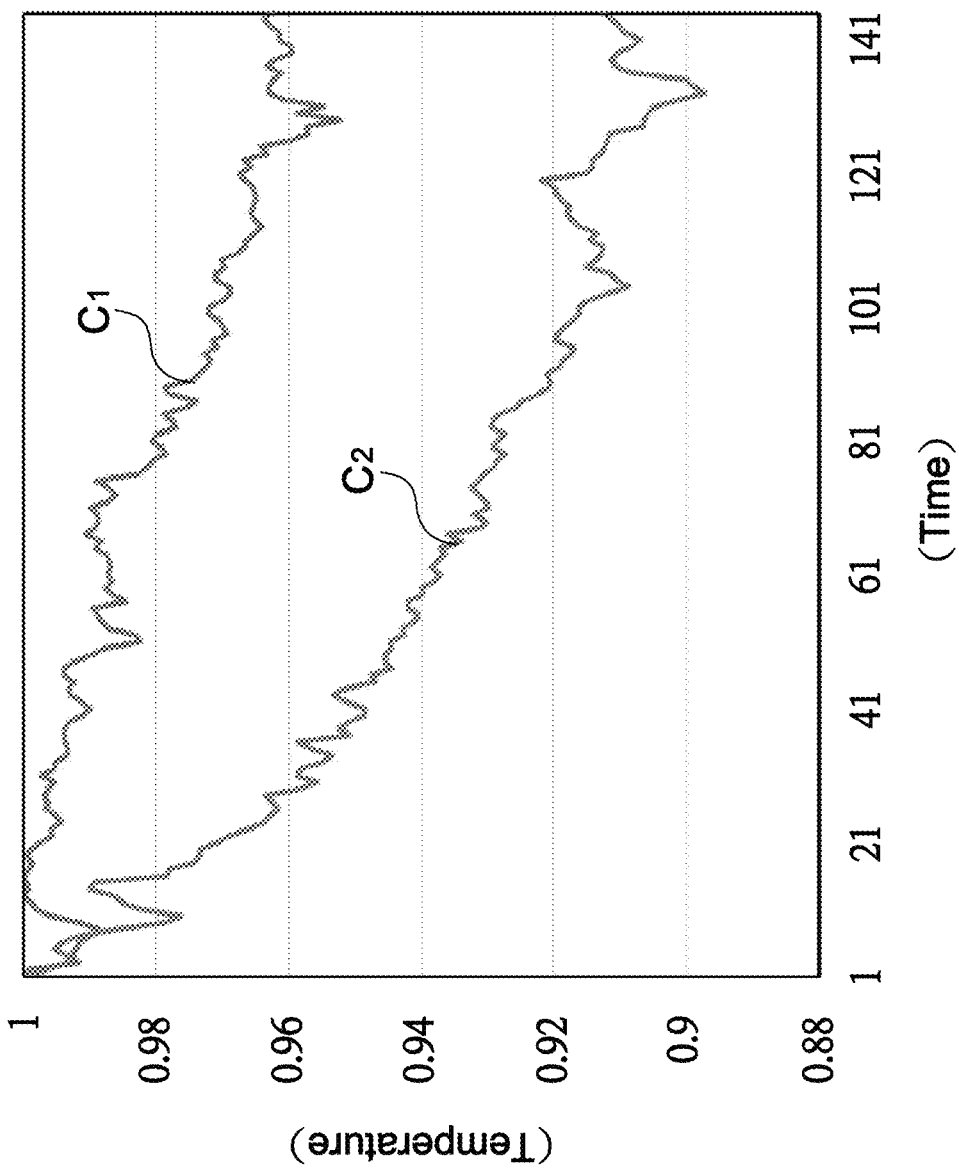

FIG. 6 is a graph diagram illustrating relations between temperature and reflex tearing and between temperature and non-reflex tearing.

DETAILED DESCRIPTION OF THE PREFERRED EMBODIMENT

Referring to FIGS. 1-6, in a preferred embodiment, the present invention includes a frame 10, a channel 20, a nozzle 30, an air supply device 40, a microcomputer 50, a thermal camera device 60 and a screen 70.

The frame 10 has at least one inner rim 11 for fixing a position of an eye E. In this embodiment, the frame 10 is a glasses frame, but the present invention is not limited to such application.

The channel 20 includes an opening 21 at an end thereof; the opening 21 is connecting the inner rim 11 of the frame 10 for the channel 20 to be fixedly connecting the frame 10.

The nozzle 30 has an exit end thereof arranged within the channel 20 toward the rim 11 of the frame 10. In this embodiment, the position of the nozzle 30 is adjustable for aligning with the position of different eyes. But the present invention is not limited to such application. The nozzle 30 can be composed of needle hose and glass syringe. When the plunger of the glass syringe is pulled up to a marked position, the plunger would start displacing back to the original position due to gravity; therefore, the weight of the plunger is the controlling factor of the wind speed of an airflow 31 sent to the eye E. In this embodiment, the nozzle 30 has an inner diameter of 0.5 mm and an inner surface area of 0.20 $mm^2$, and has a volume flow rate of 5 $cm^3$/sec and a wind speed of 2.5 m/sec. But the present invention is not limited to such application.

The air supply device 40 is connected to an entry end of the nozzle 30. In this embodiment, the air supply device 40 is either an air pump or a high-pressured air cylinder, so as to send pressured airflow 31 to cause minor irritation to the eye E, but it's not limited to such application.

The microcomputer 50 is electrically connected to the air supply device 40 for operating the air supply device 40 and the nozzle 30 to send airflow 31 from the opening 21 to the eye E, thereby producing minor irritation to the eye E to see whether there is reflex tearing reaction $R_1$ or non-reflex tearing $R_2$ reaction. In this embodiment, the microcomputer 50 has a field-programmable gate array (FPGA) and it has a broadcasting function to send instructions of opening and closing of the eye E and meanwhile operates the air supply device 40 correspondingly during the operation.

The thermal camera device 60 is arranged at an end of the channel 20 corresponding to the end with the opening 21 and has an optical camera 61 arranged toward the opening 21 for taking images of the eye E with temperature changes T thereof during the reflex tearing reaction $R_1$ or non-reflex tearing reaction $R_2$. The thermal camera device 60 is electrically connected to the microcomputer 50 for the microcomputer 50 to analyze the temperature changes T of the eye E and thereby evaluates the tear secretion A of the eye E. In this embodiment, the thermal camera device 60 records a thermal image 62 of the eye E, defining a central area $E_1$ and a surrounding area $E_2$ in accordance with the central area of the thermal image 62; the central area $E_1$ and the surrounding area $E_2$ are then memorized by the microcomputer 50 for which to detect and record an average temperature of the surrounding area $E_2$ during the operation. In the embodiment, the surrounding area $E_2$ has a diameter of 3 mm.

The screen 70 is electrically connected to the microcomputer 50 for displaying images of the eye E during the operation.

Furthermore, the operation steps of the present invention are disclosed as following.

Step 1: having a subject put on the glasses frame 10.

Step 2: having the subject keep his tested eye E opened between blinking.

Step 3: turning on the microcomputer 50.

Step 4: sending instructions to the subject of keeping his tested eye E opened for 10 seconds by broadcasting from the microcomputer 50 and recording a temperature change T of the teste eye E during the 10-second period.

Step 5: having the subject of closing his tested eye E for 10 seconds (blinking is acceptable).

Step 6: having the subject of opening his tested eye E and sending the airflow 31 to the tested eye E to cause minor irritation to the eye E.

Step 7: sending instructions to the subject of keeping his tested eye E opened for 10 seconds by broadcasting from the microcomputer 50 and recording a temperature change T of the teste eye E during the 10-second period.

After performing the operation with 10 subjects, the results of temperature changes T of the subjects are further processed with average calculation and normalization, and two graph lines $C_1$, $C_2$ of the temperature changes T are obtained as shown in FIG. 6. The graph line $C_1$ indicated the temperature change T of non-reflex tearing reaction $R_2$ with insufficient amount of tear secretion of the tested eye E, and the graph line $C_2$ indicated the temperature change T of reflex tearing reaction $R_1$ with sufficient amount of tear secretion of the tested eyes E. Thereby we can learn that those having a non-reflex tearing reaction $R_2$ cannot secrete the tears normally.

In short, with the structures disclosed above, the present invention has the following features and improvements comparing to the conventional techniques.

1. The arrangement of having the thermal camera device 60 and the nozzle 30 aligning with the frame 10 makes it easier for the subjects to fix a position of his eyes in front of the frame 10 more steadily and for the nozzle 30 and the thermal camera device 60 to perform the operation and record the temperature changes T more easily.

2. The method of sending airflows to cause minor irritations to the tested eyes E is more acceptable and preferable to the subjects rather than the conventional method of using cotton swabs to irritate the nose of the subjects and then applying test strips to the eyes. And the former is a measurable method without invasive actions.

3. There are various methods of obtaining the temperature changes of the tested eye E, including using a traditional thermal detection devices and using the thermal camera device 60. However, the thermal camera device 60 is able to record the temperature changes T more precisely with analysis of date retrieved from the images of the eyes E during the operation, while thermal detection devices can only provide a generalized information of the temperature changes T; such information may also include irrelevant data such as temperature changes of the eyelids. Therefore the information provided by the conventional thermal detection devices is not precise and correct enough.

4. The conventional method of using the test strips has to wait for 5 minutes to ensure the test strips are well infiltrated by the tears. However, the present invention has the thermal camera device 60 to replace the test strips without taking the 5 minutes period to obtain the result, since the more tears secreted, the more degree the temperature of the eyes drops. In other words, the thermal camera device 60 makes it sooner and easier to determine whether the tear secretion is well functioned or not.

5. The temperature changes are the vital factor in the operation, because normally functioned eyes has a temperature drop greater than the eyes with dry eye disease. When normally functioned eyes are irritated even slightly, there would be reflex tearing reaction $R_1$, and the abundant tears would evaporate and cause a temperature drop on the surface of the eyes. On the other hand, the eyes with dry eye disease would not secrete enough amount of tears even when encountering minor irritations. With insufficient tears in the eyes, the temperature would not change greatly.

Although particular embodiment of the invention has been described in detail for purposes of illustration, various modifications and enhancements may be made without departing from the spirit and scope of the invention. Accordingly, the invention is not to be limited except as by the appended claims.

What is claimed is:

1. An evaluation device for tear secretion, comprising:
a frame having at least one inner rim for fixing a position of an eye;
a channel including an opening at an end thereof, said opening connecting said inner rim of said frame for said channel to be fixedly connecting said frame;
a nozzle having an exit end thereof arranged within said channel toward said rim of said frame;
an air supply device connected to an entry end of said nozzle;
a microcomputer electrically connected to said air supply device for operating said air supply device and said nozzle to send airflow from said opening to the eye at said inner rim, thereby producing minor irritation to the eye to see whether there is reflex tearing or not; and
a thermal camera device arranged at an end of said channel corresponding to the end with said opening and having an optical camera arranged toward said opening for taking images of the eye with temperature changes thereof during reflex tearing reaction or non-reflex tearing reaction, said thermal camera device being electrically connected to said microcomputer for said microcomputer to analyze the temperature changes and thereby evaluate a secretion of tears of the eye.

2. The evaluation device for tear secretion as claimed in claim 1, wherein the device further including a screen to be electrically connected to the microcomputer for displaying images of the eye during the operation.

3. The evaluation device for tear secretion as claimed in claim 1, wherein the eye has a central area and a surrounding area defined in accordance with the central area, said central area and surrounding area being memorized by said microcomputer for which to detect and record an average temperature of said surrounding area during operation.

4. The evaluation device for tear secretion as claimed in claim 3, wherein the surrounding area has a diameter of 3 mm.

5. The evaluation device for tear secretion as claimed in claim 1, wherein the microcomputer has broadcasting function to send instructions of opening and closing of the eye and meanwhile operates the air supply device correspondingly during operation.

6. The evaluation device for tear secretion as claimed in claim 1, wherein the microcomputer has a field-programmable gate array.

7. The evaluation device for tear secretion as claimed in claim 1, wherein a position of the nozzle is adjustable for aligning with a position of different eyes.

8. The evaluation device for tear secretion as claimed in claim 1, wherein the air supply device is either an air pump or a high-pressured air cylinder.

9. The evaluation device for tear secretion as claimed in claim 1, wherein the frame is a glasses frame.

10. The evaluation device for tear secretion as claimed in claim 1, wherein the nozzle has an inner diameter of 0.5 mm and an inner surface area of 0.20 $mm^2$, and the nozzle has a volume flow rate of 5 $cm^3$/sec and a wind speed of 2.5 m/sec.

* * * * *